(12) United States Patent
Murase et al.

(10) Patent No.: US 6,360,581 B1
(45) Date of Patent: Mar. 26, 2002

(54) GAS SENSOR AND METHOD FOR MANUFACTURING THE SAME

(75) Inventors: Masaaki Murase; Takashi Mizukusa, both of Aichi (JP)

(73) Assignee: NGK Spark Plug Co., Ltd., Aichi (JP)

( * ) Notice: Subject to any disclaimer, the term of this patent is extended or adjusted under 35 U.S.C. 154(b) by 0 days.

(21) Appl. No.: 09/324,186

(22) Filed: Jun. 2, 1999

(30) Foreign Application Priority Data

Jun. 4, 1998 (JP) .......................................... 10-156389

(51) Int. Cl.[7] ................... G01N 27/407; G01N 27/409; G01N 27/00
(52) U.S. Cl. .................. 73/23.2; 73/23.31; 73/31.05; 204/428; 204/424; 204/431
(58) Field of Search ........................ 73/23.2, 23.31, 73/31.05; 204/424, 427, 428, 431

(56) References Cited

U.S. PATENT DOCUMENTS

| | | | | |
|---|---|---|---|---|
| 4,505,807 A | * | 3/1985 | Yamada ...................... | 204/427 |
| 4,717,464 A | * | 1/1988 | Oshima et al. ............. | 204/427 |
| 5,755,941 A | | 5/1998 | Weyl | |
| 5,880,353 A | | 3/1999 | Graser et al. | |

FOREIGN PATENT DOCUMENTS

| EP | 0 822 410 | 2/1998 | ................. 204/424 |
|---|---|---|---|
| JP | 06-3319 | * 1/1994 | |
| JP | 9-178694 | 7/1997 | |
| JP | 9-304332 | 11/1997 | |
| WO | 33165 | 9/1997 | |

\* cited by examiner

*Primary Examiner*—Daniel S. Larkin
(74) *Attorney, Agent, or Firm*—Brinks Hofer Gilson & Lione

(57) ABSTRACT

A gas sensor 1 includes a casing 10 which covers a sensing element 2 and includes two cylindrical members. The cylindrical members are axially disposed in such a manner as to overlap each other. Examples of the cylindrical members are a protector 11 (outer member) and a protector attachment portion 9a (inner member) of a metallic shell 9. A diameter-reduced portion 81 is circumferentially formed on the outer member 11 through, for example, caulking. A weld zone 83 is circumferentially formed at the diameter-reduced portion 81 so as to weld the outer member 11 onto the inner member 9a. Through formation of the diameter-reduced portion 81, a gap between the outer member 11 and the inner member 9a as measured at the position of the weld zone is reduced, thereby improving adhesion therebetween. As a result, possibility of a weld defect arising can be suppressed. Further, attainment of a good welded state does not require the practice of dimensional control of the inner and outer members; particularly, strict dimensional control of the difference between the bore diameter of the outer member and the outside diameter of the inner member. Hence, production efficiency or yield of gas sensors is improved.

11 Claims, 10 Drawing Sheets

(a)

(b)

(a)

(b)

(a)

(b)

GAS SENSOR AND METHOD FOR MANUFACTURING THE SAME

BACKGROUND OF THE INVENTION

1. Field of the Invention

The present invention relates to a gas sensor, such as an oxygen sensor, HC sensor, or NOx sensor, for detecting a component in gas to be measured.

2. Description of Related Art

Conventionally, a gas sensor is known to assume a structure in which a metallic casing accommodates a bar-like or cylindrical sensing element which has a sensing portion formed at its tip end and is adapted to detect a component in gas. The metallic casing often includes a combination of a plurality of cylindrical members, such as a metallic shell, a protector, an inner cylindrical member, and an outer cylindrical member. The metallic shell has a screw portion formed on its outer surface which is used for attachment. The protector is connected to the metallic shell in such a manner as to cover the sensing portion of a sensing element which projects from one end of the metallic shell. The inner cylindrical member is connected to the other end of the metallic shell and adapted to cover the sensing element which extends rearward from the metallic shell; i.e., opposite the protector with respect to the metallic shell. The outer cylindrical member is connected to a rear end portion of the inner cylindrical member and allows a lead wire from the sensing element to extend rearward from a rear open end thereof.

Various methods are employed for establishing a bond between the plurality of cylindrical members. For example, when an airtight bond is required, an end portion of one member is loosely fitted or press-fitted into an end portion of the other member so as to form an overlap zone. Subsequently, the overlap zone is circumferentially welded, thereby forming a circumferential weld zone.

The above conventional bonding methods involve the following problems. In the case of, for example, a loose fit between the inner and outer members, if an excessively large gap is formed between the overlapped inner and outer members, the weld zone is apt to include an incompletely welded portion, failing to attain airtightness. In the case of a press fit, if the outside diameter of the inner member is excessively large, the practice of press fitting causes the outer member to be forcibly expanded, potentially resulting in flaring of the press-fitted open end portion of the outer member. As a result, a relatively large gap is formed between the inner member and the flared end portion of the outer member, potentially failing to form a complete weld zone.

Accordingly, when the inner member and the outer member are to be welded regardless of whether they are loosely fitted or press-fitted, their dimensions must be controlled in a considerably strict manner so as to avoid formation of an excessive gap between the fitted inner and outer members. However, employment of a relatively small dimensional tolerance accompanies labor-intensive, costly process control, causing an increase in sensor cost.

SUMMARY OF THE INVENTION

The present invention provides a gas sensor comprising a bar-like or cylindrical sensing element and a cylindrical casing. The sensing element has a sensing portion formed at a tip end portion thereof and is adapted to detect a component in gas to be measured (gas under measurement). The cylindrical casing covers the sensing element while the gas under measurement is permitted to flow therethrough to the sensing portion. The casing includes at least two axially adjacent cylindrical members. An end portion of one cylindrical member (an inner member) is disposed within a corresponding end portion of the other cylindrical member (an outer member) to thereby form an overlap zone. A diameter-reduced portion is circumferentially formed on the outer member in such a manner as to be located at an axially intermediate position of the overlap zone. A weld zone is circumferentially formed at the diameter-reduced portion so as to establish an airtight bond between the outer member and the inner member.

The present invention further provides a method for manufacturing a gas sensor comprising a bar-like or cylindrical sensing element and a cylindrical casing. The sensing element has a sensing portion formed at a tip end portion thereof and is adapted to detect a component in gas to be measured (gas under measurement). The cylindrical casing covers the sensing element while the gas under measurement is permitted to flow therethrough to the sensing portion. The casing includes at least two axially adjacent cylindrical members. The method comprises the steps of: disposing an end portion of one cylindrical member (an inner member) within a corresponding end portion of the other cylindrical member (an outer member) to thereby form an overlap zone; circumferentially forming a diameter-reduced portion on the outer member in such a manner as to be located at an axially intermediate position of the overlap zone; and circumferentially forming a weld zone at the diameter-reduced portion so as to establish an airtight bond between the outer member and the inner member.

According to the above-described structure of the gas sensor and the method for manufacturing the gas sensor, the casing that covers the sensing element includes the following structural features. The two cylindrical members are disposed in such a manner as to overlap each other in the axial direction of the gas sensor. The diameter-reduced portion is circumferentially formed on the outer member and located in the overlap zone. Through formation of the diameter-reduced portion, a gap formed between the outer member and the inner member as measured at the position of the weld zone can be reduced to thereby improve adhesion between the members, so that weld defects rarely arise. Accordingly, attainment of a good welded state does not require the practice of dimensional control of the inner and outer members; particularly, strict dimensional control of the difference between the bore diameter of the outer member and the outside diameter of the inner member. Hence, production efficiency or yield of gas sensors is improved.

The diameter-reduced portion may be formed into a band-like shape having a predetermined width along the circumferential direction of the outer member. The weld zone may assume an annular form located at an widthwise intermediate position of the diameter-reduced portion and having a width narrower than that of the diameter-reduced portion. As a result, the weld zone is continuously formed within the band-like diameter-reduced portion, in which through a reduction in the gap formed between the inner and outer members, adhesion between the members is improved. Hence, the possibility of a weld defect arising is further suppressed.

The weld zone is preferably formed by laser welding because of the reduced possibility of defects. The welding method is not, however, limited to laser welding, as resistance welding, such as seam welding, may be employed.

The diameter-reduced portion may assume the form of a caulked portion. The caulked portion is formed by circumferentially caulking the outer member toward the inner member in the overlap zone of the outer member and the inner member. Through employment of caulking, adhesion between the outer member and the inner member at the diameter-reduced portion can be further improved. Thus, the weld zone can be further effectively prevented from suffering a defect.

The inner member may have a concave portion which is located in the overlap zone and circumferentially formed at a position corresponding to the diameter-reduced portion of the outer member. For example, when the diameter-reduced portion of the outer member is to assume the form of the caulked portion, caulking may be performed to such an extent that the concave portion is formed on the inner member at the corresponding position. Through formation of the concave portion, adhesion between the outer member and the inner member is further improved, thereby reducing probability of a defect arising in the weld zone.

In the above-described gas sensor, the inner member may assume the form of a metallic shell which covers the sensing element while the sensing portion projects through one end portion thereof. The outer member may assume the form of a protector connected to an open end portion of the metallic shell through which the sensing portion projects, and is adapted to cover the sensing portion while gas under measurement is permitted to flow therethrough to the sensing portion. In the case of an oxygen sensor, for example, when sensor temperature decreases, water droplets may adhere to the outer surface of the protector due to condensation. In this case, if the weld zone bonding the metallic shell and the protector has a defect, the water droplets may enter through the defect and wet the sensing portion, or may cause dirt, such as rust, to adhere to the sensing portion. However, through application of the present invention to formation of the weld zone, the weld zone is effectively prevented from suffering a defect, so that such a problem is less likely to arise.

The inner member may assume the form of an inner cylindrical member, one end of which is connected to an open end portion of the metallic shell opposite the open end portion through which the sensing portion projects, the inner cylindrical member being adapted to cover the sensing element extending rearward from the metallic shell. The outer member may assume the form of an outer cylindrical member connected to the exterior of a rear end portion of the inner cylindrical member while a lead wire from the sensing element extends out through a rear open end portion thereof. In the case of an oxygen sensor for use in an automobile, for example, the outer cylindrical member or the inner cylindrical member is exposed to the exterior of the automobile. For example, when the oxygen sensor is mounted near a suspension and tires, water is apt to splash over the exposed member. As a result, if the weld zone of the inner and outer members has a defect, water may enter through the defect into the interior of the inner cylindrical member and cause malfunction of the sensor. However, through application of the present invention to formation of the weld zone, the weld zone is effectively prevented from suffering a defect, so that such a problem is less likely to arise.

An object of the present invention is to provide a gas sensor which includes a casing having at least two welded cylindrical members and which is less susceptible to weld defects without requiring the practice of considerably strict dimensional control of the cylindrical members, as well as to provide a method for manufacturing the gas sensor.

Further objects and advantages of the present invention will become apparent by reference to the following description of the preferred embodiments and appended drawings wherein like reference numbers refer to the same component, element, or feature.

DESCRIPTION OF THE PREFERRED EMBODIMENTS

Embodiments of the present invention will be described with reference to the accompanying drawings.

Figure 1:
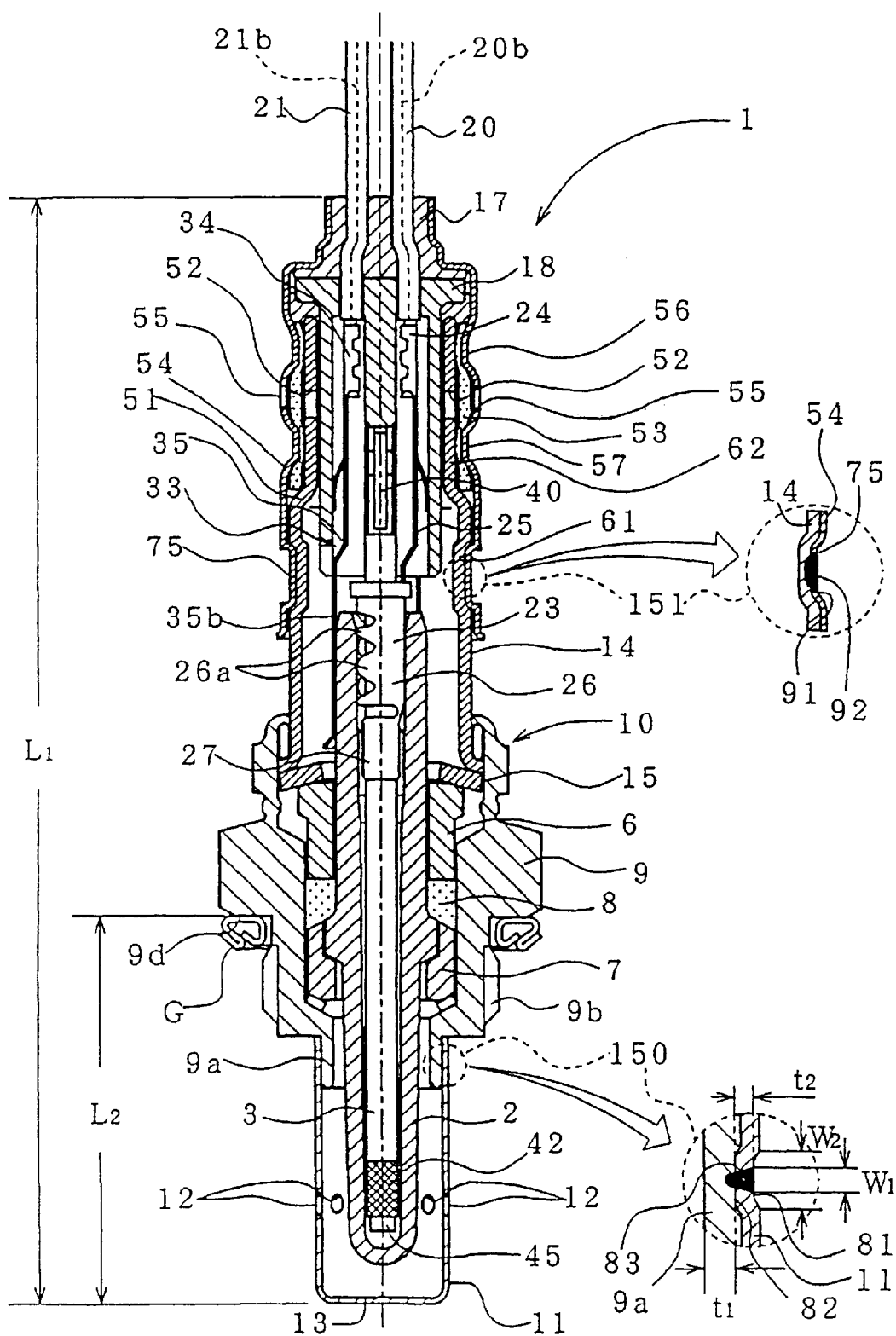
FIG. 1 is a longitudinal, full sectional view showing the internal structure of an oxygen sensor according to an embodiment of the present invention.

FIG. 1 shows the internal structure of a gas sensor according to an embodiment of the present invention. An oxygen sensor 1 shown in FIG. 1 includes an oxygen sensing element 2 and a heating member 3. The oxygen sensing element 2 is a hollow shaft-like member made of oxygen-ion conductive solid electrolyte and having a closed end. The heating member 3 is formed of a shaft-like ceramic heater. A typical example of the solid electrolyte is a solid solution of $ZrO_2$ containing $Y_2O_3$ or CaO. However, a solid solution of $ZrO_2$ and an oxide of an alkaline-earth metal or a rare-earth metal may be used. $HfO_2$ may be contained in $ZrO_2$ as a base.

Figure 2:
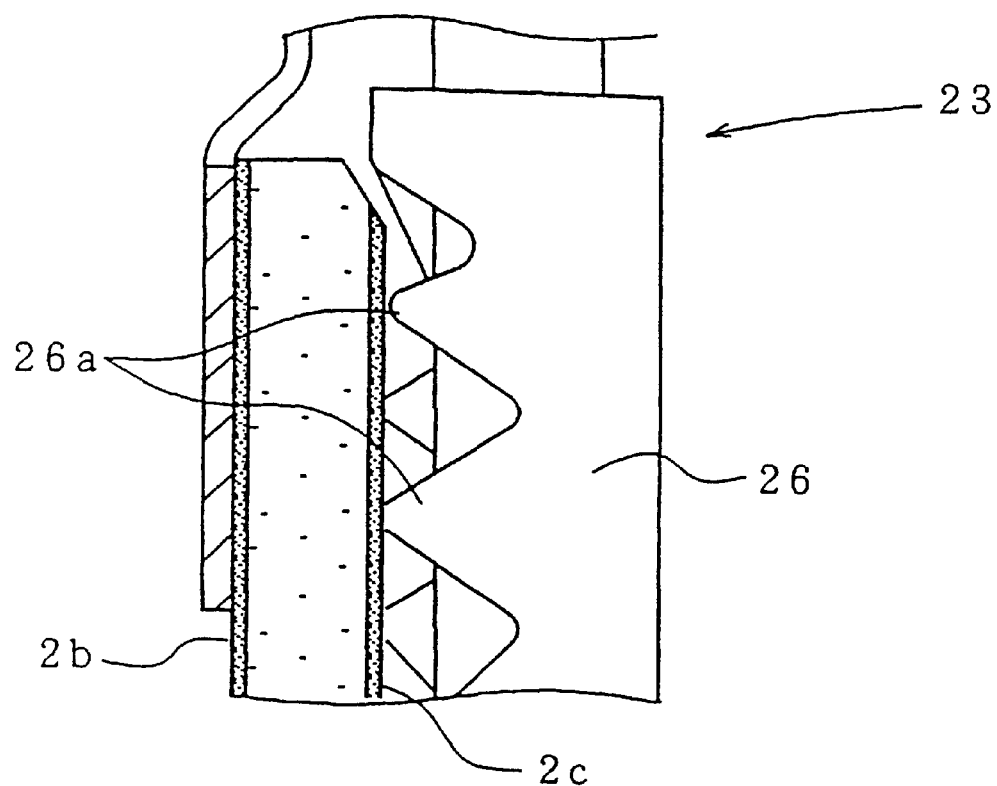
FIG. 2 is an enlarged, fragmentary, sectional view showing a portion of contact between a heating portion and an oxygen sensing element in the embodiment of FIG. 1.
Figure 2:
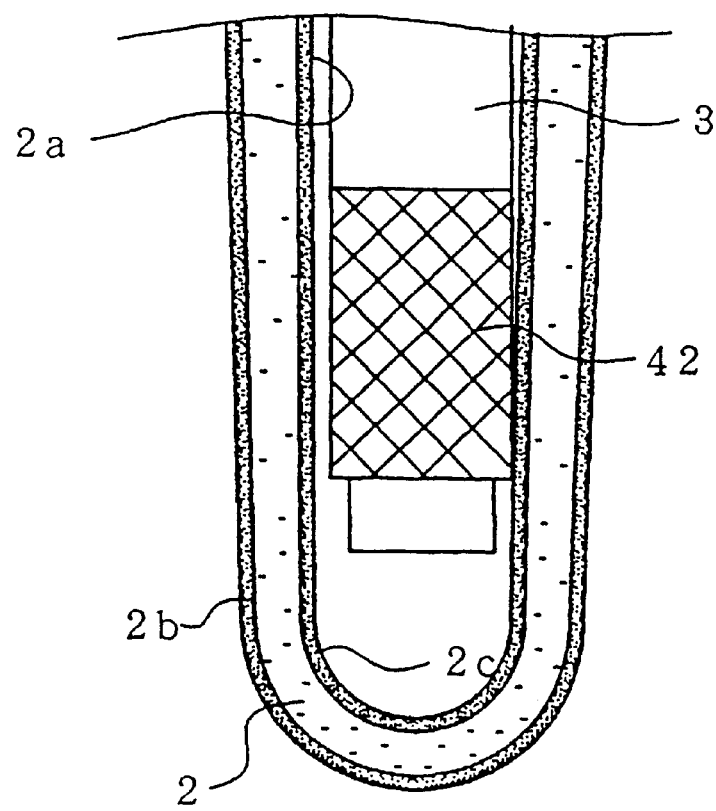

The oxygen sensing element 2 passes through a metallic casing 10 while being electrically insulated from the casing 10. Specifically, the casing 10 is disposed around the middle of the oxygen sensing element 2 in a state that insulators 6 and 7 of insulating ceramic and a ceramic powdery material 8 of talc are inserted therebetween. The casing 10 includes a metallic shell 9, an inner cylindrical member 14, and a protector 11. The metallic shell 9 includes a screw portion 9b adapted to mount the oxygen sensor 1 onto an attachment portion, such as an exhaust pipe. The inner cylindrical member 14 is connected to one open end portion of the metallic shell 9 such that the interior thereof communicates with that of the metallic shell 9. The protector 11 is connected to the other end portion of the metallic shell 9. As shown in FIG. 2, electrode layers 2b and 2c are layered entirely over the inner and outer surfaces of the oxygen sensing element 2, respectively. The electrode layers 2b and 2c are electrodes, for example, Pt porous electrodes, having a reversible catalytic function (oxygen dissociation catalytic function) in relation to a dissociation reaction of oxygen molecules for injecting oxygen into the solid electrolyte of the oxygen sensing element 2 and a recombination reaction of oxygen to cause the solid electrolyte to release oxygen.

Herein, in connection with the axial direction of the oxygen sensing element 2, the term "front" (or "tip") implies heading toward the closed extreme end of the oxygen sensing element 2, and the term "rear" (or "rear end") implies heading away from the closed extreme end.

The inner cylindrical member 14 is fitted to and caulked at the rear open end of the metallic shell 9 in a state that a ring 15 is placed between the inner cylindrical member 14 and the insulator 6. An outer cylindrical member 54 is fitted and fixed to the exterior of the inner cylindrical member 14. The upper opening of the outer cylindrical member 54 in FIG. 1 is sealed with a grommet (elastic sealing member) 17 of, for example, rubber. Further, a ceramic separator 18 is located under and adjacent to the grommet 17 within the outer cylindrical member 54. Lead wires 20 and 21 connected to the oxygen sensing element 2 and lead wires (located behind the lead wires 20 and 21 and thus not visible) connected to the heating member 3 are provided passing through the ceramic separator 18 and the grommet 17.

The lead wire 20 is electrically connected to the inner electrode layer 2c (FIG. 2) of the oxygen sensing element 2 through a connector portion 24 of a terminal member 23, a lead-out strip portion 25, and an internal electrode connecting portion 26 of the terminal member 23. The lead wire 21 is electrically connected to the outer electrode layer, not shown, of the oxygen sensing element 2 through a connector portion 34, a lead-out strip portion 35 connected to the connector portion 34, and an external electrode connecting portion 35b of another terminal member 33.

When the exhaust gas temperature is sufficiently high, the oxygen sensing element 2 is heated by the exhaust gas, so that it is activated. When the exhaust gas is at low temperature upon engine startup, for example, the oxygen sensing element 2 is forcibly heated by the heating member 3 to be activated. The heating member 3 is usually a ceramic heater. In the ceramic heater, a ceramic bar 45 made mainly of alumina is used as a core member. A heating portion 42 is formed on a tip portion of the ceramic bar 45. The heating portion 42 includes a resistor wire part (not shown) patterned in a zigzag fashion, for example. Current is fed to the resistor wire part through a lead wire extending from a heater terminal 40, thereby heating a tip portion (sensing portion) of the oxygen sensing element 2 to a predetermined activation temperature or higher.

The heating member 3 is held within a hollow portion of the oxygen sensing element 2 by means of the terminal member 23. The terminal member 23 includes a heating member holding portion 27 located at the side of the tip of the heating member 3 with respect to the internal electrode connecting portion 26 (i.e., at the near side with respect to the heating portion 42). The heating member holding portion 27 is shaped in a letter C in cross section to surround the heating member 3. The heating member holding portion 27 has an internal diameter slightly smaller than the external diameter of the heating member 3 when the heating member 3 is not inserted thereinto. When the heating member 3 is inserted into the heating member holding portion 27, the internal diameter of the heating member holding portion 27 elastically expands to thereby hold the heating member 3 by means of a frictional force exerted therebetween. The heating member holding portion 27 is provided at only one axial end of the internal electrode connecting portion 26.

In order to form the internal electrode connecting portion 26, a blank sheet portion having saw-tooth contact parts 26a formed at opposite side edges are bent into a cylindrical form, which may surround the heating member 3. The internal electrode connecting portion 26 functions to axially position the heating member 3 within the hollow portion of the oxygen sensing element 2 by means of a frictional force exerted between the outer surface of the heating member 3 and an inner wall 2a of the hollow portion. Electrical connection with the inner electrode layer 2c (FIG. 2) is established by means of tip portions of the contact parts 26a.

As shown in FIG. 1, the external cylindrical member 54 is coaxially connected to the exterior of a rear portion of the inner cylindrical member 14 (casing 10). The inner cylindrical member 14 includes a stepped portion 51 formed at a rear end portion thereof. The inner cylindrical member 14 further includes a first portion 61 formed at the axially front side of the stepped portion 51 and a second portion 62 formed at the axially rear side of the stepped portion 51. The diameter of the second portion 62 is smaller than that of the first portion 61. The second portion 62 has a plurality of gas inlet holes 52 circumferentially formed therein. A cylindrical filter 53 is disposed around the second portion 62 in such a manner as to cover the gas inlet holes 52. The filter 53 is covered with the outer cylindrical member 54. The outer cylindrical member 54 has a plurality of auxiliary gas inlet holes 55 formed therein such that the auxiliary gas inlet holes 55 are located at a position corresponding to the filter 53 and circumferentially arranged at predetermined intervals. The outer cylindrical member 54 includes annular filter-caulked portions 56 and 57 formed at the rear and front sides, respectively, of a row of auxiliary gas inlet holes 55 so as to fixedly press fit the filter 53 in cooperation with the second portion 62 of the inner cylindrical member 14.

The outer cylindrical member 54 is disposed to overlap the first portion 61 of the inner cylindrical member 14 from outside. At the overlap portion, a caulked portion 75 is formed on the outer cylindrical member 54 so as to join the outer cylindrical member 54 onto the inner cylindrical member 14.

The filter 53 is a water-repellent filter of a porous fibrous structure (for example, Gore-Tex (product of Japan Gore-Tex)). Such a porous fibrous structure is obtained by stretching an unfired compact of, for example, polytetrafluoroethylene (PTFE) in at least one axial direction at a heating temperature lower than the melting point of PTFE. The water-repellent filter prevents penetration of liquid which mainly contains water, but permits penetration of gas such as air and/or water vapor. Through employment of the water-repellent filter, air as a reference gas is introduced into the inner cylindrical member 14 (casing 10) through the auxiliary gas inlet holes 55, the filter 53, and the gas inlet holes 52, while liquid-phase water is prevented from entering into the inner cylindrical member 14.

A cylindrical protector attachment portion 9a is formed at a front open end portion of the metallic shell 9. A cap-shaped protector 11 is attached onto the protector attachment portion 9a in such a manner as to cover a tip portion (sensing portion) of the oxygen sensing element 2 with a predetermined space intervening therebetween. A plurality of gas holes 12 through which exhaust gas passes are formed in a wall portion of the protector 11 and circumferentially arranged at predetermined intervals. A gas hole 13 is also formed in a bottom portion of the protector 11. The gas holes 12 and 13 enable oxygen in exhaust gas to contact the surface of a tip portion of the oxygen sensing element 2.

The protector attachment portion 9a (inner member) is axially inserted into a cylindrical open end portion of the protector 11 (outer member), thereby forming an overlap zone. In the overlap zone, a band-shaped caulked portion (diameter-reduced portion) 81 is circumferentially formed on the protector 11, while a band-shaped concave feature 82 is formed on the protector attachment portion at a position corresponding to the caulked portion 81. The inner surface of the caulked portion 81 of the protector 11 is in close contact with the surface of the band-shaped concave feature 82 of the protector attachment portion 9a.

In the band-shaped caulked portion 81, an annular weld zone 83 is formed at a widthwise intermediate position of the caulked portion 81 in such a manner as to be narrower than the caulked portion 81. The weld zone 83 extends between the protector 11 and the protector attachment portion 9a to thereby airtightly weld them. Hereinafter, a combined joint structure of a caulked portion and a weld zone is called a caulked, welded structure, and a combined joint structure of the caulked portion 81 and the weld zone 83 is called a caulked, welded structure 150.

Figure 3:
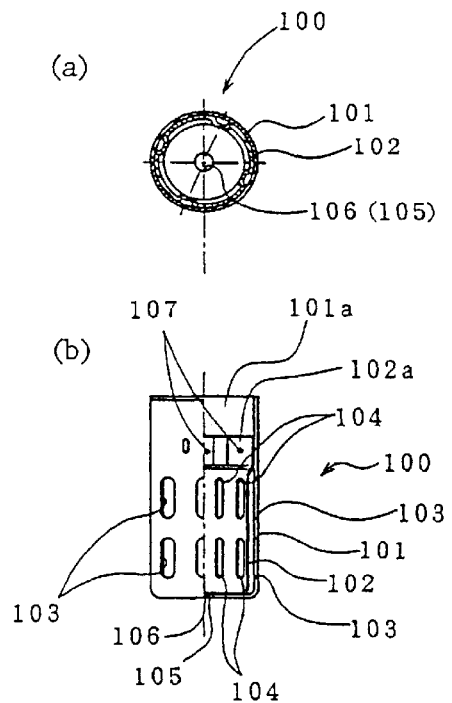
FIG. 3(a) is a plan view in full section of an example protector.
FIG. 3(b) is a front, elevational view in half section showing an example protector.

The protector 11 of FIG. 1 is a single-wall structure. However, a double-wall structure as shown in FIGS. 3(a) and 3(b) may be employed. A protector 100 of FIGS. 3(a) and 3(b) includes a closed-bottomed first cylindrical member 101 and a closed-bottomed second cylindrical member 102 which is concentrically disposed within the first cylindrical member 101 with a predetermined gap formed therebetween. An open end portion of the second cylindrical member 102 is expanded in diameter in such a manner as to fit the bore of the first cylindrical member 101, thereby forming a flared portion 102a. The flared portion 102a is circumferentially spot-welded to the first cylindrical member 101, thereby forming spot weld zones 107. The axial length of the second cylindrical member 102 is shorter than that of the first cylindrical member 101. The second cylindrical member 102 is disposed within the first cylindrical member 101 such that an open end of the flared portion 102a is receded into the first cylindrical member 101 by a predetermined distance as measured from an open end of the first cylindrical member 101. Thus, a socket portion 101a having a predetermined axial length is formed at an open end portion of the first cylindrical member 101 so as to receive the protector attachment portion 9a.

A plurality of elongated gas holes 103 are formed in a wall portion of the first cylindrical member 101. The gas holes 103 are circumferentially arranged at predetermined intervals and in two rows which are axially apart from each other. Similarly, two rows of gas holes 104 are formed in a wall portion of the second cylindrical member 102. In order to prevent entry of water droplets, the positions of the gas holes 104 are circumferentially shifted from those of the gas holes 103. A bottom portion of the second cylindrical member 102 is in close contact with that of the first cylindrical member 101. A gas hole 105 is formed in the bottom portion of the first cylindrical member 101 at the center thereof, while a gas hole 106 is formed in the bottom portion of the second cylindrical member 102 at the center thereof. The gas holes 105 and 106 are allowed to communicate with each other.

Figure 4:
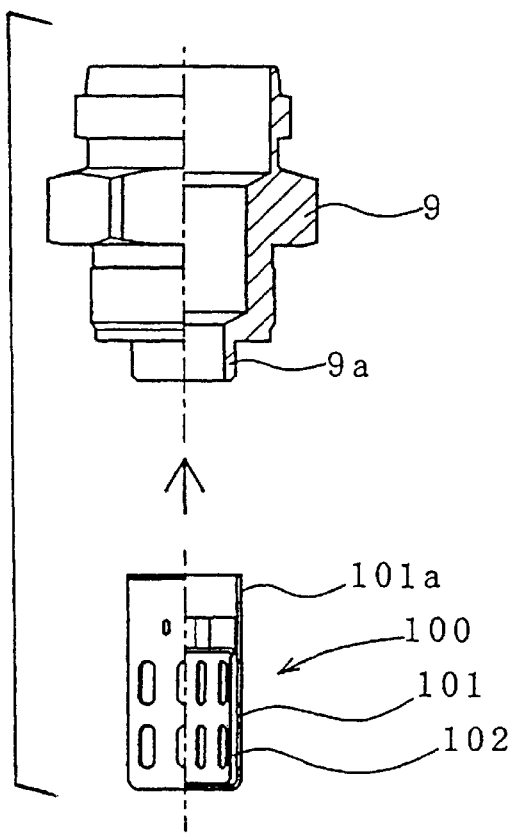
FIG. 4 is a front, elevational view in half section depicting a step of bonding of a protector and a metallic shell in the form of a caulked, welded structure.
Figure 5:
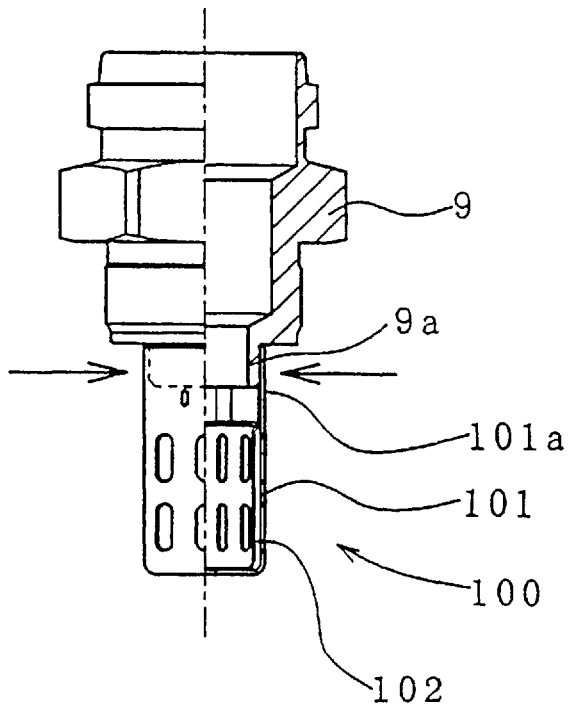
FIG. 5 is a front, elevational view in half section depicting a step subsequent to that of FIG. 4.
Figure 6:
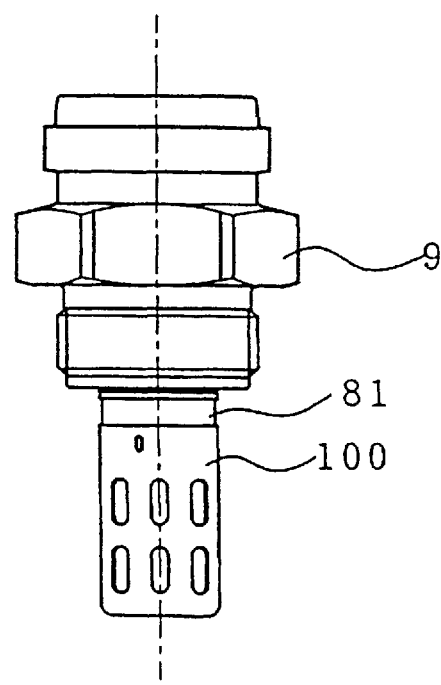
FIG. 6 is a front, elevational view depicting a step subsequent to that of FIG. 5.

The caulked, welded structure 150 can be formed by, for example, a process as depicted in FIGS. 4, 5, 6, 7(a), and 7(b). (These figures exemplify the protector 100 of a double-wall structure as shown in FIGS. 3(a) and 3(b). However, the process is also applicable to the case of the protector 11 of a singlewall structure as shown in FIG. 1.) Specifically, as shown in FIG. 4, the protector attachment portion 9a of the metallic shell 9 is inserted into the socket portion 101a of the protector 100 until the open end of the socket portion 110a abuts a stepped-end surface of the metallic shell 9. Next, as shown in FIG. 5, an axially intermediate part of the socket portion 110a is circumferentially caulked toward the protector attachment portion 9a, thereby forming a caulked portion 81, as shown in FIG. 6. As a result of formation of the caulked portion 81, the band-shaped concave feature 82 is formed on the protector attachment portion 9a at the corresponding position as shown in FIG. 1, thereby establishing strong adhesion between the socket portion 101a and the protector attachment portion 9a.

The caulked portion 81 and the concave feature 82 are formed through plastic deformation of the socket portion 101a and the protector attachment portion 9a, respectively, which accompanies caulking. However, for example, only the caulked portion 81 is formed through plastic deformation of the socket portion 101a, while the protector attachment portion 9a substantially undergoes elastic deformation. In this case, the concave feature 82 is not explicitly formed on the protector attachment portion 9a at a position corresponding to the caulked portion 81. However, mainly through an elastically restoring force of the protector attachment portion 9a, strong adhesion can also be established between the socket portion 101a and the protector attachment portion 9a.

Figure 11:
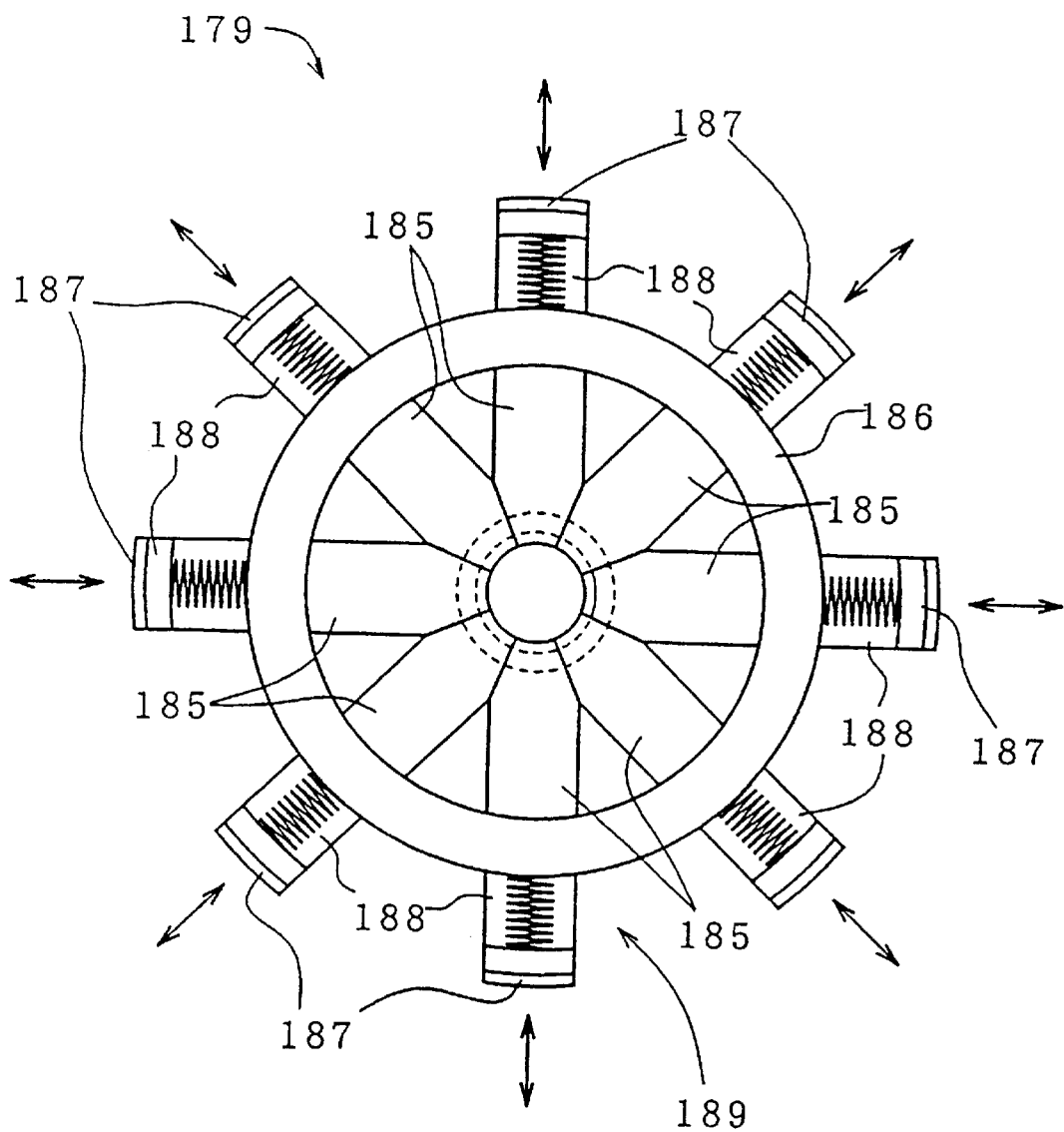
FIG. 11 is a schematic, plan view showing a main portion of a caulker.
Figure 12:
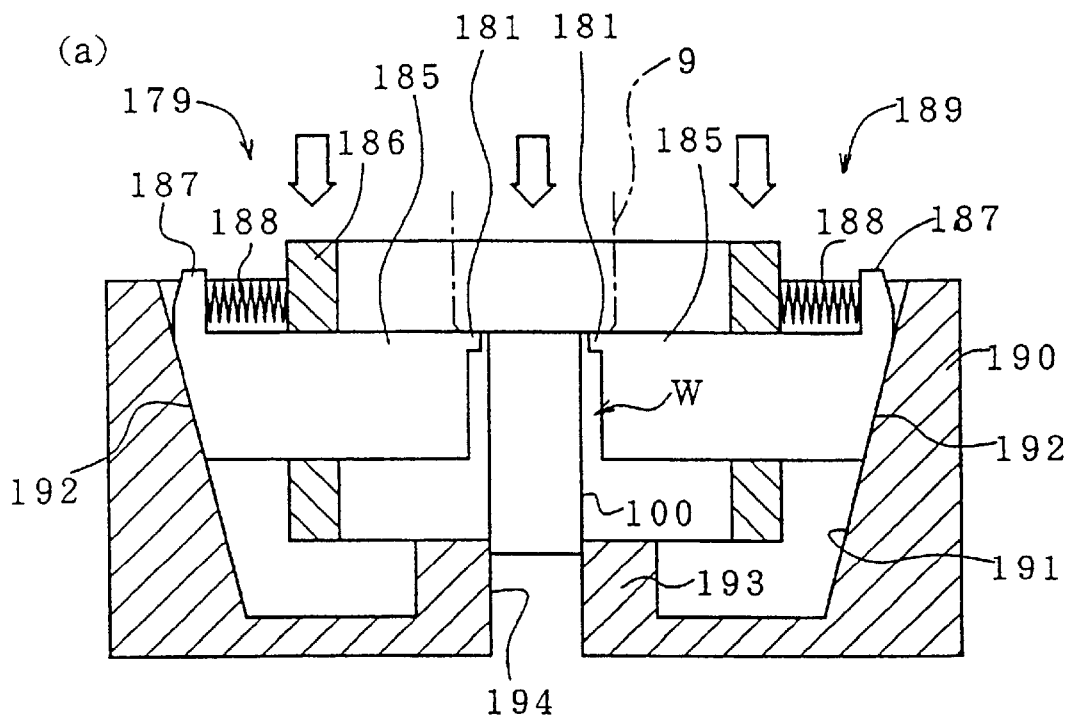
FIGS. 12(a) and 12(b) are schematic, sectional side view showing the main portion of the caulker of FIG. 11 and depicting action of the caulker.
Figure 12:
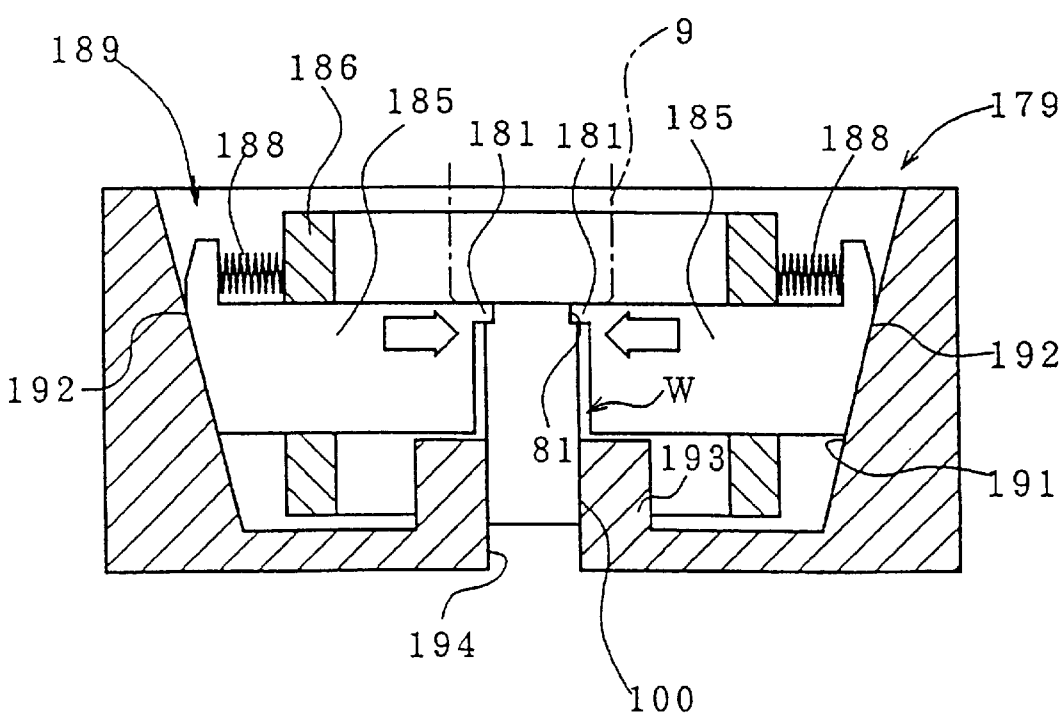

FIG. 11 is a plan view showing an example caulker. A caulker 179 includes a punch assembly 189, which, in turn, includes a punch holder 186 of ring shape and a plurality of punch segments 185. The punch segments 185 are circumferentially arranged on the punch holder 186 and extend through the punch holder 186 in a radially reciprocative manner. A spring support 187 is formed at a rear end portion of each punch segment 185. A spring member 188 is disposed between the spring support 187 and the outer circumferential surface of the punch holder 186. As shown in FIG. 12(a), the caulker 179 further includes a receive unit 190 which cooperatively works with the punch assembly 189. An inner wall 191 of the receive unit 190 is tapered such that a diameter defined by the inner wall 191 reduces toward the bottom of the receive unit 190. A positioning projection 193 is formed on the bottom at the center and has a workpiece insertion hole 194 formed therein.

A workpiece W is set in the caulker 179 such that a tip portion of the protector 100 is inserted into the workpiece insertion hole 194. The punch assembly 189 is coaxially set within the receive unit 190, so that the punch segments 185 surround a base portion (socket portion 110a) of the protector 100 to be caulked. An outer end surface 192 of each punch segment 185 is tapered so as to correspond to the inner wall 191 of the receive unit 190.

In this state, while the workpiece W is pressed axially downward, the punch assembly 189 is pressed downward toward the bottom of the receive unit 190. As a result, as shown in FIG. 12(b), because of cam action induced between the tapered outer end surfaces 192 and the inner wall 191, the punch segments 185 approach the workpiece W and compression of the corresponding springs 188 occurs. Thus, through action of a caulking portion 181 formed at the tip of each punch segment 185, the caulked portion 81 is formed on the protector 100.

Figure 7:
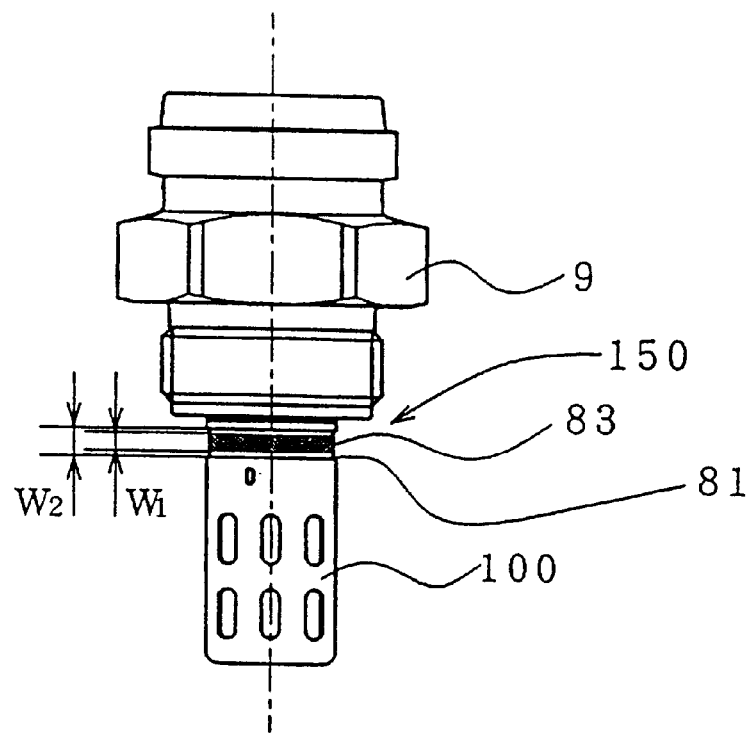
FIG. 7(a) is a front, elevational view depicting a step subsequent to that of FIG. 6.
FIG. 7(b) is an enlarged, fragmentary sectional, view of a portion of FIG. 7(a)
Figure 7:
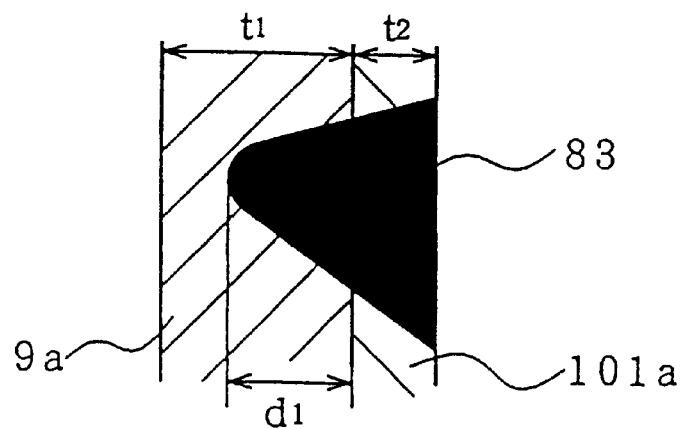

Next, as shown in FIG. 7(a), the caulked portion 81 is subjected to, for example, laser welding to thereby form the circumferential weld zone 83 and obtain the caulked, welded structure 150. Where W1 represents the width of the weld zone 83 and W2 represents the width of the caulked portion 81, ratio W1/W2 is preferably not less than 0.5 in order to secure a required bonding strength (in the example of FIG. 1, W1 is about 0.7 mm, W2 is about 1 mm, and W1/W2 is about 0.7). In order to sufficiently exert a caulking force on the protector attachment portion 9a (inner member) so as to establish good contact under pressure, thickness t2 of the socket portion 101a (outer member) is preferably not greater than 1 mm (in the example of FIG. 1, t2 is about 0.4 mm). Further, penetration d1 of the weld zone 83 into the protector attachment portion 9a (inner member) is preferably not less than 0.4 mm in order to secure a required bonding strength. However, if the weld zone 83 extends through the thickness of the protector attachment portion 9a (inner member), bonding strength may deteriorate due to weld defects. Thus, penetration d1 is preferably smaller than thickness t1 of the protector attachment portion 9a.

Figure 8:
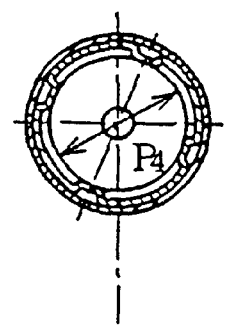
FIG. 8(a) is an explanatory plan view in full section showing dimensions of a protector.
FIG. 8(b) is an explanatory front, elevational view in half section showing dimmensions of a protector.
Figure 8:
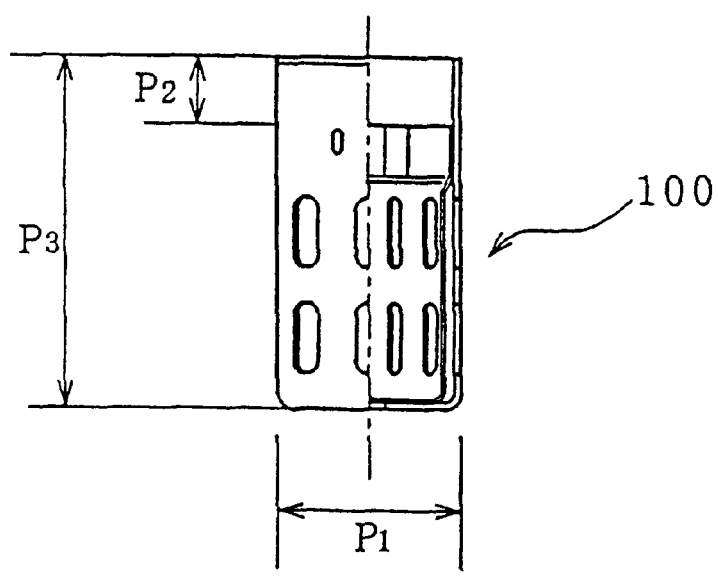

Dimensions of the protector 100 shown in FIGS. 8(a) and 8(b) may be set, for example, as follows (parenthesized dimensions are specific ones of the protector 100 of FIGS. 3(a) and 3(b)).
P1: 9.8–12 mm (10.35 mm)
P2: 3.9–4.9 mm (3.9 mm)
P3: 12.9–20.2 mm (20 mm)
P4: 7.4–8.1 mm (7.7 mm)

Figure 9:
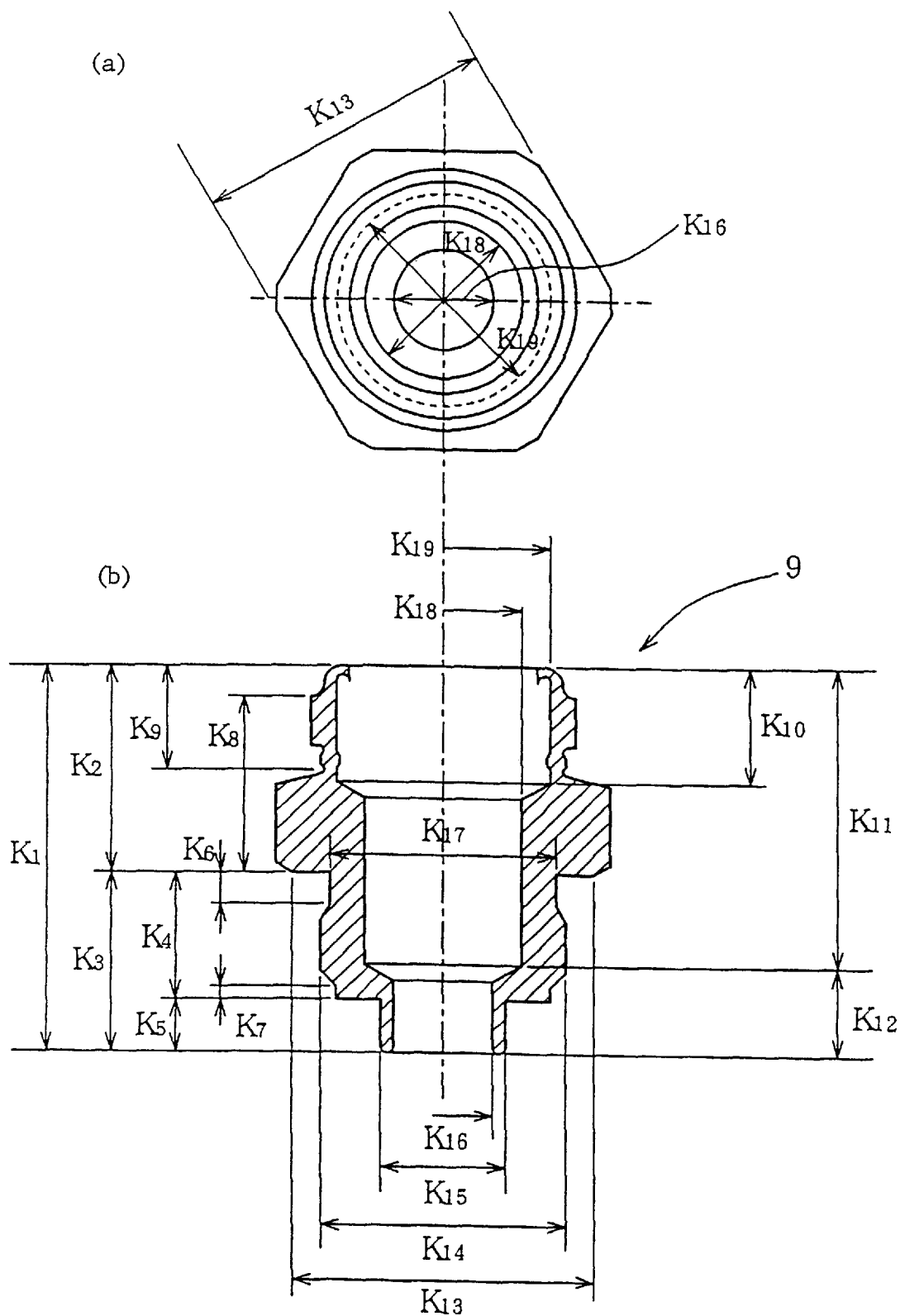
FIG. 9(a) is an explanatory top plan view showing dimensions of a metallic shell.
FIG. 9(b) is an explanatory longitudinal, full sectional view showing dimensions of a metallic shell.

Dimensions of the metallic shell 9 shown in FIGS. 9(a) and 9(b) may be set, for example, as follows (parenthesized dimensions are specific ones of the metallic shell 9 of FIG. 1).
K1: 25–30 mm (29.6 mm)
K2: 13–17 mm (16.8 mm)
K3: 12.5–13.0 mm (12.8 mm)
K4: 8.8–9.2 mm (9 mm)
K5: 3.6–4 mm (3.8 mm)
K6: 1–2.5 mm (2 mm)
K7: 0.5–1.5 mm (1 mm)
K8: 12–14 mm (13.9 mm)
K9: 7–10 mm (9.6 mm)
K10: 7.5–10.5 mm (10 mm)
K11: 20.6–23.6 mm (23.1 mm)
K12: 6–7 mm (6.5 mm)
K13: 21.8–22.2 mm (22 mm)
K14: for example, M18
K15: 9.3–11.2 mm (9.5 mm)
K16: 7.3–7.7 mm (7.5 mm)
K17: 16.3–16.7 mm (16.5 mm)
K18: 11.4–11.8 mm (11.6 mm)
K19: 15.8–16.2 mm (16 mm)

In FIG. 1, the overall length L1 of the sensor 1 is about 84 mm. Length L2 between a seat surface 9d for gasket G of the metallic shell 9 and the tip surface of the protector 11 is about 29 mm.

Operation of the oxygen sensor 1 will next be described.

In the thus-constructed oxygen sensor 1, air as base gas is introduced thereinto through the filter 53 provided within the outer cylindrical member 54. Exhaust gas is introduced through the gas holes 12 of the protector 11 and comes in contact with the outer surface of the oxygen sensing element 2. As a result, an electromotive force is generated in the oxygen sensing element 2 by the oxygen concentration cell effect. The generated electromotive force depends on the oxygen concentration difference between the interior and the exterior of the oxygen sensing element 2. The electromotive force is lead out through the lead wires 20 and 21 from the electrode layers 2b and 2c, in the form of a detection signal representative of the oxygen concentration contained in the exhaust gas, thereby determining the oxygen concentration in the exhaust gas.

As described previously, the caulked, welded structure 150 is formed between the protector 11 and the protector attachment portion 9a of the metallic shell 9. Specifically, the caulked portion 81 is previously formed in the overlap zone between the protector 11 and the protector attachment portion 9a to thereby improve adhesion therebetween. Then, the weld zone 83 is circumferentially formed at the caulked portion 81, thereby effectively preventing a defect arising in the weld zone 83 and improving airtightness of bond. For example, when the temperature of the oxygen sensor 1 decreases, water droplets may adhere to the outer surface of the protector 11 due to condensation. In this case, if the weld zone 83 to bond the metallic shell 9 and the protector 11 has a defect, the water droplets may enter through the defect and wet the sensing portion, or may cause dirt, such as rust, to adhere to the sensing portion. However, through employment of the caulked, welded structure 150 for bonding the metallic shell 9 and the protector 11, such entry of water droplets or dirt, for example, can be effectively prevented.

In the case of a conventional process in which the protector 11 and the protector attachment portion 9a are loosely fitted or press-fitted together, followed by formation of a weld zone, dimensional control must be carried out in a considerably strict manner over the protector 11 and the protector attachment portion 9a; particularly, the difference between the bore diameter of the protector 11 and the outside diameter of the protector attachment portion 9a. However, through employment of the caulked, welded structure 150, even when some dimensional variations exist at the stage of fitting, formation of the caulked portion 81 establishes a state of close contact. Thus, the conventionally required strict dimensional control is not required, thereby improving production efficiency or yield of gas sensors.

Alternatively, a diameter-reduced portion of a band-like shape may be circumferentially formed at an open base end portion of the protector 11 by, for example, press work. Subsequently, the protector attachment portion 9a of the metallic shell 9 is press-fitted into the diameter-reduced portion. Then, a weld zone is formed at the diameter-reduced portion to thereby bond the protector 11 and the protector attachment portion 9a. Through press fitting of the protector attachment portion 9a into the diameter-reduced portion, the open end portion of the protector 11 hardly becomes flared, so that probability of a defect arising in the weld zone can be reduced. In this case, the concave feature 82 is not explicitly formed on the protector attachment portion 9a.

Also, in the oxygen sensor 1 of FIG. 1, an annular weld zone 92 may be formed at the caulked portion 75 for joining the inner cylindrical member 14 and the outer cylindrical member 54, thereby forming a caulked, welded structure 151. As a result, airtightness of the joint between the inner cylindrical member 14 and the outer cylindrical member 54 can be further improved. Notably, an annular concave feature 91 is formed on the inner cylindrical member 14, corresponding to the caulked joint 75.

Figure 10:
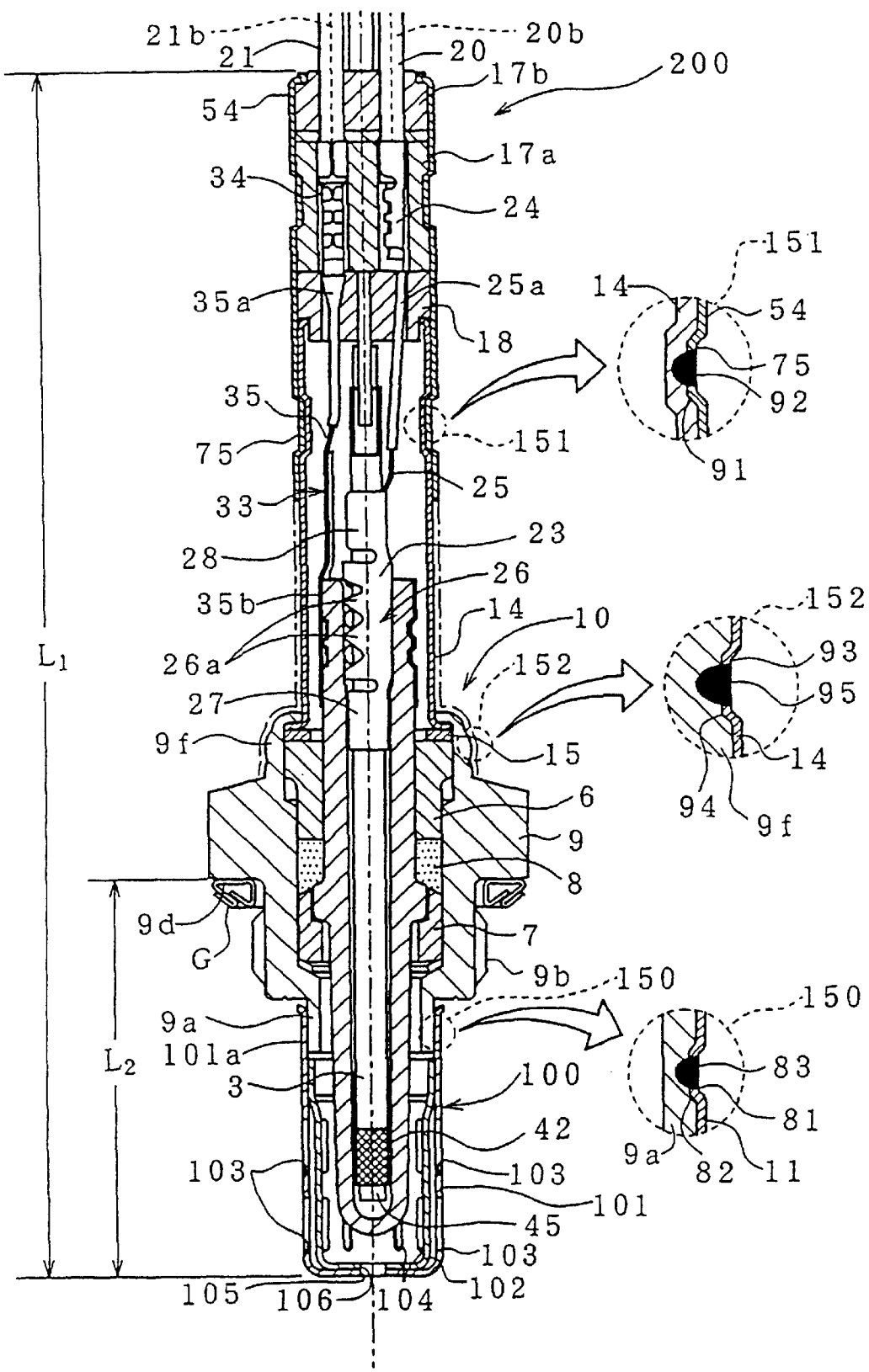
FIG. 10 is a longitudinal, full sectional view showing a modified embodiment of the oxygen sensor of FIG. 1.

FIG. 10 shows an oxygen sensor according to another embodiment of the present invention. In an oxygen sensor 200 of FIG. 10, a grommet fitted into an open end portion of an outer cylindrical member 54 includes a first grommet 17b (of, for example, fluororubber) located closer to the open end and a second grommet 17a (of, for example, silicone rubber). Air as base gas is introduced into the interior of the inner cylindrical member 14 through a gap formed between a core wire 20b (21b) of the lead wire 20 (21) and a resin sheath surrounding the core wire 20b (21b). A member corresponding to the filter 53 of FIG. 1 is not provided. A terminal member 23 includes heating member holding portions 27 and 28 located at axially opposite ends of an internal electrode connecting portion 26. Reference numerals 25a and 35a denote insulating tubes which cover lead wires 25 and 35, respectively. Other structural features are substantially identical to those of the oxygen sensor 1 of FIG. 1 and thus are denoted by common reference numerals, and detailed description thereof is omitted. The sensor 200 of FIG. 10 is shown on a scale identical to that of FIG. 1. L1 is about 92 mm, and L2 is about 29 mm.

The outer cylindrical member 54 may be extended until it covers an inner cylindrical member connecting portion 9f projecting from a rear end portion of the metallic shell 9, thereby forming an overlap zone. In the overlap zone, a caulked, welded structure 152 including a caulked portion 93 (a concave feature 94 is formed on the inner cylindrical member connecting portion 9f) and a weld zone 95 may be formed.

The above-described sensor structure of the present invention is similarly applicable to a gas sensor other than an oxygen sensor, such as an HC sensor or NOx sensor.

The foregoing disclosure is the best mode devised by the inventors for practicing this invention. It is apparent, however, that apparatus and methods incorporating modifications and variations will be obvious to one skilled in the art of gas sensors. Inasmuch as the foregoing disclosure presents the best mode contemplated by the inventors for carrying out the invention and is intended to enable any person skilled in the pertinent art to practice this invention, it should not be construed to be limited thereby but should be construed to include such aforementioned obvious variations and be limited only by the spirit and scope of the following claims.

What is claimed is:

1. A gas sensor comprising:
   a sensing element having a sensing portion formed at a tip end portion thereof and adapted to detect a component of a gas under measurement; and
   a cylindrical casing covering the sensing element while the gas under measurement is permitted to flow therethrough to the sensing portion;
   said casing including at least one inner cylindrical member and at least one outer axially adjacent cylindrical member; an end portion of the one inner cylindrical member disposed within a corresponding end portion of the one outer cylindrical member to thereby form an overlap zone; a circumferential diameter-reduced portion formed on the outer member in such a manner as to be located at an axially intermediate position of the overlap zone; and a weld zone circumferentially formed at the diameter-reduced portion so as to establish an airtight bond between the outer member and the inner member.

2. A gas sensor according to claim 1, wherein the diameter-reduced portion is a band-like shape having a predetermined width along the circumferential direction of the outer member; and the weld zone is an annular form located at a widthwise intermediate position of the diameter-reduced portion having a width narrower than that of the diameter-reduced portion.

3. A gas sensor according to claim 1, wherein the weld zone is formed by laser welding.

4. A gas sensor according to claim 1, wherein the diameter-reduced portion is a caulked portion formed by circumferentially caulking the outer member toward the inner member in the overlap zone of the outer member and the inner member.

5. A gas sensor according to claim 1, wherein the inner member has a concave feature which is located in the overlap zone and circumferentially formed at a position corresponding to the diameter-reduced portion of the outer member.

6. A gas sensor according to claim 1, wherein the inner member is a metallic shell covering the sensing element, the sensing portion projects through one end portion thereof; and
   the outer member is a protector connected to an open end portion of the metallic shell through which the sensing portion is projected, and adapted to cover the sensing portion while gas under measurement is permitted to flow therethrough to the sensing portion.

7. A gas sensor according to claim 1, wherein the cylindrical casing further includes a metallic shell covering the sensing element, the sensing portion projects through one end portion thereof;
   the inner member is an inner cylindrical member, one end of which is connected to an open end portion of the metallic shell opposite the open end portion through which the sensing portion projects, the inner cylindrical member being adapted to cover said sensing element extending rearward from the metallic shell; and
   the outer member is an outer cylindrical member connected to the exterior of a rear end portion of the inner cylindrical member while a lead wire from said sensing element extends out through a rear open end portion thereof.

8. The gas sensor according to claim 1 wherein the sensing element is bar-like.

9. The gas sensor according to claim 1 wherein the sensing element is cylindrical.

10. A method for manufacturing a gas sensor comprising a sensing element and a cylindrical casing, the sensing element having a sensing portion formed at a tip end portion thereof and adapted to detect a component in gas under measurement, the cylindrical casing covering the sensing element while the gas under measurement is permitted to flow therethrough to the sensing portion, the casing including at least an inner cylindrical member and at least an outer axially adjacent cylindrical member, said method comprising the steps of:
   disposing an end portion of the inner cylindrical member within a corresponding end portion of the outer cylindrical member to thereby form an overlap zone;
   circumferentially forming a diameter-reduced portion on the outer member in such a manner as to be located at an axially intermediate position of the overlap zone; and
   circumferentially forming a weld zone at the diameter-reduced portion so as to establish an airtight bond between the outer member and the inner member.

11. A method for manufacturing a gas sensor according to claim 10, wherein the outer member is circumferentially caulked toward the inner member in the overlap zone of the outer member and the inner member to thereby form a caulked portion serving as the diameter-reduced portion; and the weld zone is circumferentially formed at the caulked portion.

* * * * *